(12) United States Patent
Casalini

(10) Patent No.: US 11,040,247 B2
(45) Date of Patent: Jun. 22, 2021

(54) REAL-TIME AND DYNAMICALLY GENERATED GRAPHICAL USER INTERFACES FOR COMPETITIVE EVENTS AND BROADCAST DATA

(71) Applicant: Technogym S.p.A., Cesena (IT)

(72) Inventor: Filippo Casalini, Parma (IT)

(73) Assignee: TECHNOGYM S.p.A., Cesena (IT)

( * ) Notice: Subject to any disclaimer, the term of this patent is extended or adjusted under 35 U.S.C. 154(b) by 0 days.

(21) Appl. No.: 16/289,243

(22) Filed: Feb. 28, 2019

(65) Prior Publication Data

US 2020/0276475 A1 Sep. 3, 2020

(51) Int. Cl.
*A63B 24/00* (2006.01)
*A63B 71/06* (2006.01)

(52) U.S. Cl.
CPC ...... *A63B 24/0062* (2013.01); *A63B 71/0622* (2013.01); *A63B 2024/0065* (2013.01); *A63B 2024/0068* (2013.01); *A63B 2230/04* (2013.01)

(58) Field of Classification Search
None
See application file for complete search history.

(56) References Cited

U.S. PATENT DOCUMENTS

| | | | |
|---|---|---|---|
| 5,215,468 | A | 6/1993 | Lauffer et al. |
| 5,616,104 | A | 1/1997 | Mulenburg et al. |
| 6,050,924 | A | 4/2000 | Shea |
| 6,450,922 | B1 | 9/2002 | Henderson et al. |
| 6,902,513 | B1 | 6/2005 | McClure |
| 7,651,423 | B2 | 1/2010 | Ichida et al. |

(Continued)

FOREIGN PATENT DOCUMENTS

| | | |
|---|---|---|
| AT | 505617 A4 | 3/2009 |
| CN | 101842138 A | 9/2010 |

(Continued)

OTHER PUBLICATIONS

"Search Report" and "Written Opinion," Italian Patent Application No IT201600083062, dated Apr. 21, 2017, 5 pages (7 pages including English Translation).

(Continued)

*Primary Examiner* — James S. McClellan
*Assistant Examiner* — Peter J Iannuzzi
(74) *Attorney, Agent, or Firm* — Carr & Ferrell LLP

(57) ABSTRACT

Real-time and dynamically generated graphical user interfaces for competitive events and broadcast data are disclosed herein. An example method includes determining, for each of a plurality of individuals, at least one of an absolute performance threshold or a personal performance threshold; receiving a data feed from each of a plurality of workout devices associated with the plurality of individuals over a network, the data feed including at least one of real-time absolute performance data or real-time personal performance data; determining, for each of the individuals, a performance zone based on a comparison of at least one of the real-time absolute performance data and the absolute performance threshold or the real-time personal performance data and the personal performance threshold; generating a graphical user interface that includes a broadcast of a real-time video of an instructor leading a workout; and a real-time leaderboard overlaid on the broadcast.

20 Claims, 7 Drawing Sheets

(56) References Cited

U.S. PATENT DOCUMENTS

| | | |
|---|---|---|
| 10,272,280 B2 | 4/2019 | Leonardi et al. |
| 10,576,348 B1 | 3/2020 | Hawkins, III et al. |
| 10,799,755 B2 | 10/2020 | Cristofori et al. |
| 10,888,736 B2 | 1/2021 | Fedriga |
| 2003/0040348 A1 | 2/2003 | Martens |
| 2003/0171190 A1 | 9/2003 | Rice |
| 2006/0003872 A1 | 1/2006 | Chiles et al. |
| 2006/0084551 A1 | 4/2006 | Volpe, Jr. |
| 2006/0234840 A1 | 10/2006 | Watson et al. |
| 2007/0281828 A1 | 12/2007 | Rice |
| 2008/0103030 A1 | 5/2008 | Watson et al. |
| 2008/0207402 A1 | 8/2008 | Fisher et al. |
| 2009/0011907 A1 | 1/2009 | Radow et al. |
| 2009/0118099 A1 | 5/2009 | Fisher et al. |
| 2009/0118100 A1 | 5/2009 | Oliver et al. |
| 2009/0217780 A1 | 9/2009 | Evett |
| 2009/0227429 A1 | 9/2009 | Baudhuin |
| 2010/0113223 A1 | 5/2010 | Chiles et al. |
| 2010/0292600 A1* | 11/2010 | Dibenedetto .......... A61B 5/024 600/520 |
| 2011/0118086 A1 | 5/2011 | Radow et al. |
| 2011/0196519 A1 | 8/2011 | Khoury et al. |
| 2012/0238406 A1 | 9/2012 | Beard et al. |
| 2013/0059698 A1 | 3/2013 | Barton |
| 2014/0171266 A1 | 6/2014 | Hawkins, III et al. |
| 2014/0224055 A1 | 8/2014 | Cracco et al. |
| 2014/0361511 A1 | 12/2014 | Thompson |
| 2014/0378280 A1 | 12/2014 | Kristiansen et al. |
| 2015/0080190 A1 | 3/2015 | Kaan et al. |
| 2015/0228262 A1 | 8/2015 | Silfvast et al. |
| 2015/0290490 A1 | 10/2015 | Badarneh |
| 2015/0344103 A1 | 12/2015 | Kuroda |
| 2015/0344104 A1 | 12/2015 | Kuroda |
| 2016/0236751 A1 | 8/2016 | Rosen |
| 2016/0266867 A1 | 9/2016 | Olesh et al. |
| 2016/0311483 A1 | 10/2016 | Laronde |
| 2017/0334518 A1 | 11/2017 | Bortoli et al. |
| 2018/0001142 A1 | 1/2018 | Viarani et al. |
| 2018/0036586 A1 | 2/2018 | Cristofori et al. |
| 2018/0043206 A1 | 2/2018 | Crist et al. |
| 2018/0056132 A1* | 3/2018 | Foley ................ A63B 24/0087 |
| 2018/0126248 A1* | 5/2018 | Dion .................... H04L 65/403 |
| 2018/0126249 A1* | 5/2018 | Consiglio .......... A63B 71/0619 |
| 2018/0140903 A1* | 5/2018 | Poure ................ A63B 24/0062 |
| 2019/0143194 A1* | 5/2019 | Evancha ............ H04N 21/4415 482/4 |
| 2020/0009444 A1* | 1/2020 | Putnam ................ A61B 5/7435 |
| 2020/0147449 A1 | 5/2020 | Liu et al. |
| 2020/0269090 A1 | 8/2020 | Fedriga |
| 2020/0272311 A1 | 8/2020 | Rotta |

FOREIGN PATENT DOCUMENTS

| | | | |
|---|---|---|---|
| CN | 102893063 A | 1/2013 | |
| CN | 107684696 A | 2/2018 | |
| CN | 107684696 B | 6/2020 | |
| EP | 2564904 A1 | 3/2013 | |
| EP | 2571280 A2 | 3/2013 | |
| EP | 2703051 A2 | 3/2014 | |
| EP | 2949367 A1 | 2/2015 | |
| EP | 3278842 A2 | 2/2018 | |
| EP | 3278842 A3 | 6/2018 | |
| EP | 3278842 B1 | 7/2020 | |
| EP | 3698855 A1 * | 8/2020 | .......... A63B 21/005 |
| EP | 3698856 A1 | 8/2020 | |
| EP | 3703068 A1 | 9/2020 | |
| IT | 102016000083062 A1 | 8/2016 | |
| TW | 201808403 | 6/2017 | |
| WO | WO1987001953 A1 | 4/1987 | |
| WO | WO1992020408 A1 | 11/1992 | |
| WO | WO2008002644 A2 | 1/2008 | |
| WO | WO200903170 A1 | 12/2008 | |
| WO | WO2018035117 A1 | 2/2018 | |

OTHER PUBLICATIONS

"Office Action," Chinese Patent Application No. 201710662848.4, dated Jan. 21, 2019, 8 pages (15 pages including English Translation).

"Extended European Search Report", European Patent Application No. EP20159062.7, dated Jun. 16, 2020, 6 pages.

"Extended European Search Report", European Patent Application No. EP20158332.5, dated Jun. 26, 2020, 8 pages.

"Extended European Search Report", European Patent Application No. EP20159696.2, dated Jul. 13, 2020, 15 pages.

Goode, Lauren, "My Two-Month Ride with Peloton, the Cultish, Internet-Connected Fitness Bike," The Verge [online], Apr. 25, 2017, [retrieved on Jul. 1, 2020], Retrieved from the Internet: <URL:https://www.theverge.com/2017/4/25/15408338/bike-peleton-review-indoor-cycle-live-streaming-cycling>, 10 pages.

"Notice of Allowance", European Patent Application No. 17184196.8, dated Jul. 2, 2020, 2 pages.

* cited by examiner

| COLOR CODE | SPEED RANGE REFERENCE (km/h) |
|---|---|
| COLOR 1 (e.g. purple) | greater than 12 |
| COLOR 2 (e.g. brown) | from 10 to 12 |
| COLOR 3 (e.g. green) | from 8 to 10 |
| COLOR 4 (e.g. yellow) | from 6 to 8 |
| COLOR 5 (e.g. pink) | less than 6 |

| COLOR CODE | POWER RANGE REFERENCE (Watt) |
|---|---|
| COLOR 1 (e.g. yellow) | greater than 210 |
| COLOR 2 (e.g. brown) | from 180 to 210 |
| COLOR 3 (e.g. pink) | from 150 to 180 |
| COLOR 4 (e.g. green) | from 110 to 150 |
| COLOR 5 (e.g. purple) | less than 110 |

REAL-TIME AND DYNAMICALLY GENERATED GRAPHICAL USER INTERFACES FOR COMPETITIVE EVENTS AND BROADCAST DATA

CROSS REFERENCE TO RELATED APPLICATIONS

N/A

FIELD OF THE INVENTION

The present disclosure generally pertains to systems and methods that provide interactive graphical user interfaces that generate and display real-time competitive data along with broadcast video feeds.

SUMMARY

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a method comprising determining, for at least one individual, at least one of an absolute performance threshold or a personal performance threshold; receiving at least one of real-time absolute performance data or real-time personal performance data for the at least one individual; determining, for the at least one individual, a performance zone based on at least one of a combination of the real-time absolute performance data and the absolute performance threshold or a combination of the real-time personal performance data and the personal performance threshold; generating for display on a graphical user interface: a real-time leaderboard overlaid on a broadcast, the real-time leaderboard comprising a relative listing of the at least one individual based on the performance zone of the at least one individual relative to other individuals competing with the at least one individual, each entry of the relative/relative/ranked listing comprising at least a visual indication of the performance zone.

Another general aspect includes a system comprising a processor and memory, the processor being configured to execute instructions stored in the memory to determine, for each of a plurality of individuals, at least one of an absolute performance threshold or a personal performance threshold; receive a data feed from each of a plurality of workout devices associated with the plurality of individuals over a network, the data feed comprising at least one of real-time absolute performance data or real-time personal performance data; determine, for each of the individuals, a performance zone based on at least one of a combination of the real-time absolute performance data and the absolute performance threshold or a combination of the real-time personal performance data and the personal performance threshold; and transmit a graphical user interface that comprises: a broadcast of a real-time video of an instructor leading a workout; and a real-time leaderboard overlaid on the broadcast, the real-time leaderboard comprising a relative listing of the individuals based on the performance zone of the individuals, each entry of the relative/ranked listing comprising a visual indication of the performance zone providing an instantaneous indication of relative performance of the individuals and indicate potential upcoming changes in leaderboard positioning.

According to some embodiments, the present disclosure is directed to an example method comprising: assessing a performance zone for each of a plurality of individuals using an assessment routine executed on a plurality of workout devices coupled with an orchestration service over a network, the performance zone being based on one or more of an absolute performance percentage and a personal performance percentage; generating a graphical user interface that comprises: a broadcast of a real-time video of an instructor leading a workout; and a real-time leaderboard overlaid on the broadcast, the real-time leaderboard comprising a relative listing of their individuals based on their respective performance zone, each entry of the relative/ranked listing comprising a visual indication of the performance zone providing an instantaneous indication of relative performance of the individuals and indicating potential upcoming changes in leaderboard positioning; and simulcasting the graphical user interface to a plurality of workout devices.

BRIEF DESCRIPTION OF THE DRAWINGS

The accompanying drawings, where like reference numerals refer to identical or functionally similar elements throughout the separate views, together with the detailed description below, are incorporated in and form part of the specification, and serve to further illustrate embodiments of concepts that include the claimed disclosure, and explain various principles and advantages of those embodiments.

The methods and systems disclosed herein have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

DETAILED DESCRIPTION

Figure 1:
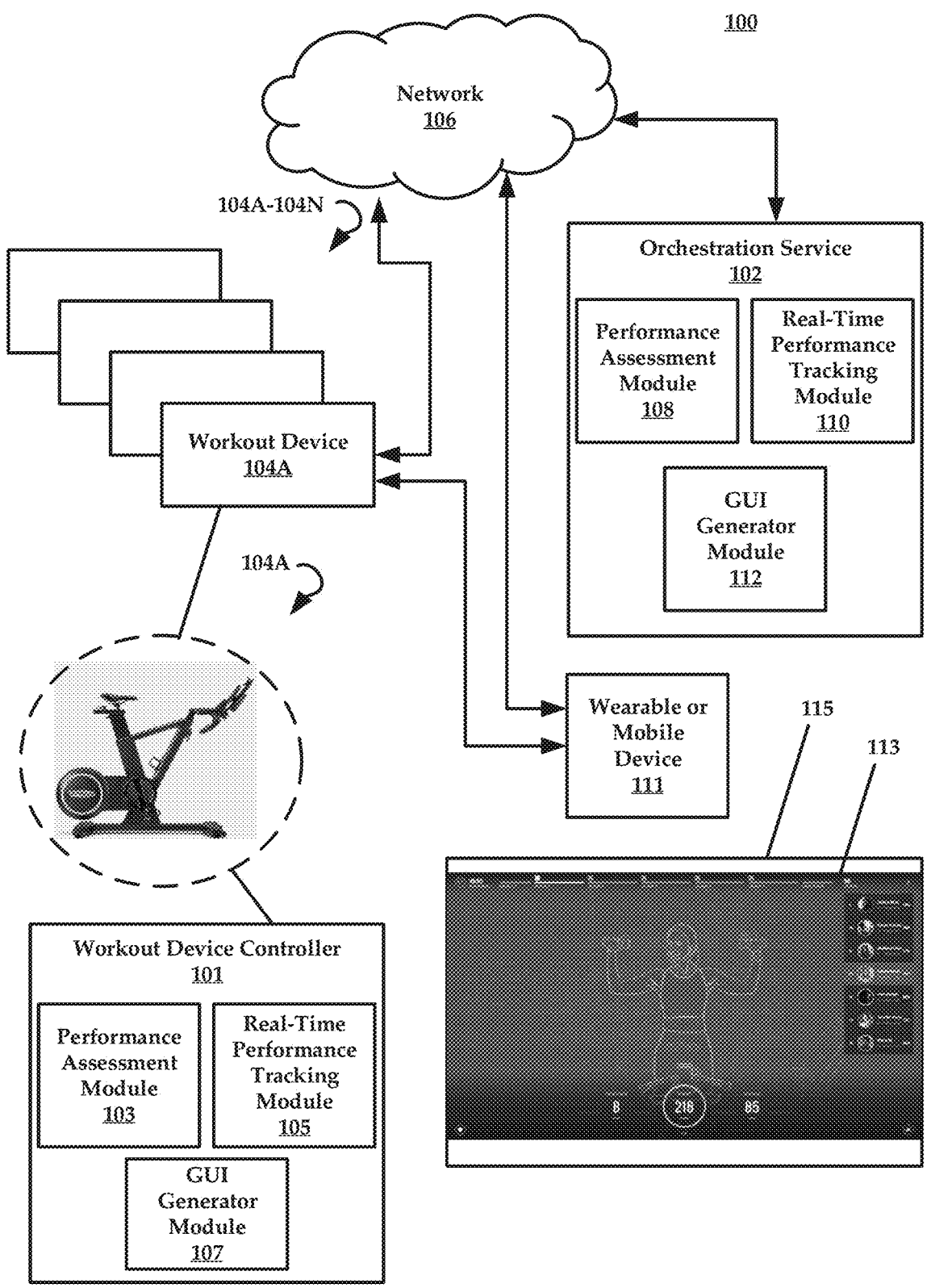
FIG. 1 is a schematic diagram of an example environment where aspects and embodiments of the present disclosure can be performed.

Generally speaking, the present disclosure is directed to systems and methods that provide an interactive workout platform that provides dynamic graphical user interfaces that include real-time updated leaderboards for workout events. In some embodiments, the workout events include live, broadcasted video feeds where trainers facilitate workout events for remote participants. For example, a trainer conducts a workout with a plurality of individuals in their homes, where each of the individuals is using a workout device that can transmit data in real-time to an orchestration service.

The broadcasted data provided by the orchestration service is simulcast or otherwise accessible to a plurality of workout devices allowing for group competition between a plurality of individuals. The broadcasted data can be displayed within a graphical user interface (generated by the workout device) that comprises metrics regarding an individual's real-time physical performance in a competitive event as determined by the orchestration system. In an example use case, each of a plurality of individuals is participating in a competitive event that includes a bicycle ride. The individuals are each using, for example, a spin bike or other similar indoor, stationary bicycle (could also include an outdoor bicycle that is used in combination with another piece of equipment that allows for use indoors). The competitive event could include a race or a workout routine that is facilitated by a trainer. In one embodiment, a broadcast of a real-time video of an instructor leading a workout is simulcast or otherwise transmitted to this plurality of bicycles. In some embodiments, this can include a display screen of a smart stationary bicycle, a mobile device of an individual, a tablet computer, a laptop computer, or a television—just to name a few.

In addition to the broadcast of trainer video, the graphical user interface can comprise a dynamic and real-time leaderboard. In general, the leaderboard comprises a relative listing of individuals (workout participants) based on the performance zone of the individuals. In some instances, each entry of the relative/ranked listing comprises a visual indication of the performance zone providing an instantaneous indication of relative performance of the individuals and indicates potential upcoming changes in leaderboard positioning. In some instances, performance zones are determined relative to absolute performance metrics or personal performance metrics, as will be discussed in greater detail herein.

It will be understood that while the examples disclosed herein are applicable to stationary bicycles, the present disclosure is not so limited and can be utilized in any competitive event where a plurality of individuals are competing or participating in an athletic event such as rowing, running, and the like. Thus, regardless of the context, aspects of the present disclosure can be applied as long as one or more types of performance parameters of the individuals can be collected.

To be sure, conventional exercise machines do not display sufficient and effective information about the performance metrics of the users participating in a workout or training session. Actually, the information available on the display on some exercise machines includes only information related to the real time users ranking. As a consequence, there remains an unmet need in the art to provide an exercise machine that shows valuable and useful information to the user, so as to improve class training in terms of experience and effectiveness. These and other advantages of the present disclosure are provided herein with reference to the collective drawings.

FIG. 1 is a schematic representation of an example environment 100 where aspects of the present disclosure are practiced. The environment 100 generally comprises an orchestration service 102, a plurality of workout devices 104A-104N (an example perspective view of a stationary bicycle is illustrated in a lower left portion of FIG. 1 for context), which are communicatively coupled through a network 106. The network 106 may include any one or a combination of multiple different types of networks, such as cable networks, the Internet, cellular networks, wireless networks, and other private and/or public networks. In some instances, the network 106 may include Wi-Fi or Wi-Fi direct.

It will be understood that while some embodiments disclose the use of the orchestration service 102 for data analysis and leaderboard generation, each of the plurality of workout devices 104A-104N can also be configured similarly such that the orchestration service 102 is providing only the broadcast or simulcast data of the workout trainer. In other embodiments, the plurality of workout devices 104A-104N perform each aspect of the methods disclosed herein other than the storage of absolute and/or personal performance data, which can be requested by the plurality of workout devices 104A-104N as needed.

In general, the plurality of workout devices 104A-104N can include additional or fewer workout devices than those illustrated. In one embodiment, the workout devices include stationary bicycles. Each of the plurality of workout devices 104A-104N is operated by a unique individual. In some embodiments, the plurality of workout devices 104A-104N can be located remotely from one another such as in the individual's home, or could be co-located in a workout facility or other similar location.

In some embodiments, as individuals are using the plurality of workout devices 104A-104N, each of the plurality of workout devices 104A-104N generates or tracks performance data. The performance data that is generally referred to as performance parameters in some embodiments. In one or more embodiments, the performance parameters can comprise data such as power output, heart rate, and heart rate percentage. Some performance parameters relate to physical or biometric values of the individual such as heart rate, and some performance parameters relate to the workout device, such as power output. Generally, there are two categories of performance parameters that include absolute performance parameters and personal performance parameters. Additional details on the collection and processing of these various types of performance parameters are provided in greater detail infra. These performance data are collected and transmitted to the orchestration service 102 in real-time or near-real-time in some embodiments. In some embodiments, these data are used directly in comparative calculations at the workout device level.

In various embodiments, the workout device 104A comprises a workout device controller ("controller 101") which comprises a performance assessment module 103, a real-time performance tracking module 105, and a graphical user interface generator module 107. These modules can be stored in memory and executed by a processor in some embodiments.

Generally, the performance parameters are determined based on an initial determination of various performance thresholds for an individual. The performance thresholds can be based on any one or combination of performance types. As noted above, two example types of performance types include absolute performance and personal performance.

In general, absolute performance comprises data having values that do not depend on an individual's physical fitness but reflect equipment operating parameters or the like. Non-limiting examples of absolute performance data include, for bicycles: speed, rpm, resistance (usually shown in levels, based on the amount of the braking force on the flywheel), power or combinations thereof. With respect to a treadmill, absolute performance data can include speed, cadence, power, or any combination thereof. With respect to a rower, absolute performance data can include resistance (usually showed in levels (from 1 to 1.0), based on the amount of the braking force on the flywheel), SPM (strokes per minute), power, or combinations thereof. With respect to a boxing station, absolute performance data can include punches per minute, punch power, and/or combinations thereof. These absolute performance data are instantaneous (e.g., real-time or near-real-time) values obtained during an exercise workout that are monitored (by specific sensors of the workout device or from a wearable as discussed herein) and collected (stored in a memory for comparison and/or for displaying).

According to some embodiments, personal performance data depend on an individual's physical fitness (or even on the individual's physical effort). Non-limiting examples of personal performance data include a heartrate relative to an established absolute performance level (e.g. with reference to the bike, the resistance level: at the same resistance level, individuals may have different heart rate, depending on their physical fitness or training level). Another example of personal performance data includes a maximum heart rate that can be determined by a specific test or it can be estimated by a formula: 220 minus an individual's age. Yet another example of personal performance data includes FTP (Functional Threshold Power), which represents the individual's ability to sustain a highest possible power output expressed in watts for at least 45 seconds. The FTP can be determined by considering the 90% of the maximum average power sustainable during a maximal 20 minute test.

The absolute performance thresholds and personal performance thresholds are utilized as reference or baseline values when performing real-time assessments. For example, the controller 101 of the workout device 104A can be configured to determine (on an individual basis) a performance zone based on either (1) a comparison of the real-time absolute performance data relative to the absolute performance threshold or (2) a comparison of the real-time personal performance data relative to the personal performance threshold.

In some embodiments, the performance assessment module 103 is configured to determine any one of the absolute and personal performance thresholds for an individual, as well as collect real-time absolute performance data and personal performance data during exercises. These determinations are referred to respectively as an absolute performance differential and a personal performance differential, with each being expressed as a percentage. The following examples provide non-limiting use cases for calculating and using various absolute performance data and/or personal performance data.

One example performance assessment related to personal performance includes calculating V02 max value for each individual. The V02 max value can be calculated by the performance assessment module 103 of the controller 101. For context, V02 max, also known as maximal oxygen uptake, a measurement of the maximum amount of oxygen a person can utilize during intense exercise. It is a measurement used to establish an aerobic endurance of an athlete prior to or during the course of training.

In some embodiments, the VO2 max of an individual can be calculated by the performance assessment module 103 using a VO2 max algorithm. In one example calculation, the performance assessment module 103 obtains an average wattage (average power output generated by the individual on their workout device) and this number is multiplied by 10.8. This resultant product is divided by the individual's weight in kilograms. Adding seven to this resulting value produces an estimated VO2 max. Other methods for obtaining, directly or indirectly, VO2 max can likewise be utilized. If known, an individual can enter their VO2 max into a display or interface 115 provided on their workout device, such as workout device 104A as an example. Other methods for calculating or estimating VO2 max can also be utilized.

The VO2 max is used as the basis for performance assessment module 103 to calculate additional values or metrics such as heart rate percentage. In one or more embodiments, a heart rate percentage is a value that corresponds to a current measurement of an individual's heart rate relative to their VO2 max (also referred to aerobic threshold).

According to other embodiments, rather than using V02 max, the performance assessment module 103 can utilize other performance assessment types such as estimating a maximum heart rate using bodyweight and a standard coefficient value of 45. For example, in one example estimation an individual's bodyweight is reduced by 45 to obtain an estimated maximum heart rate. Thus, if the bodyweight is 250 pounds, the maximum heart rate estimation would be 205 bpm (beats per minute). In some embodiments, an individual could enter their bodyweight into an interface 115 on their workout device 104A. The estimated maximum heart rate can be calculated locally at the workout device by the performance assessment module 103 or alternatively at the orchestration service 102. Once an estimated or actual maximum heart rate is calculated for the individual, the maximum heart rate can be stored in a user profile for the individual for later use in a database.

During a workout, performance data are collected such as real-time heart rate (an example type of personal performance data) and a real-time power output (an example type of absolute performance data). These data can be collected by the workout device 104A or by a mobile device or wearable utilized by the individual. For example, the workout device 104A can comprise sensors in the handlebars of the bicycle that collected heart rate data.

In general, real-time personal performance data are a measure of the work being performed by the individual on the workout device 104A. For example, if the workout device 104A is a bicycle, the power output is measured in watts or revolutions per minute (RPM). In general, the power output is measurement of work performed on a workout device by an individual.

In one example, using the maximum heart rate, the real-time performance tracking module 105 of the controller 101 can compare the real-time heart rate with the maximum heart rate (an example personal performance threshold) and calculate the heart rate percentage. In one example, if the maximum heart rate is 190 BPM and the real-time heart rate is 150 BPM, the heart rate percentage would be approximately 79%. Other parameters of performance can be assessed by the controller 101 as well such as cadence (measured in RPM), distance, and other similar metrics that are indicative of performance. These values can vary over time as the individual's performance parameters vary.

In other embodiments, rather than, or in addition to, receiving performance data from the workout device 104A, these data can be received from a wearable device or mobile device 111 on the individual. For example, the individual can wear a heart rate monitor device that transmits heart rate data over a Wi-Fi connection to the controller 101 of the workout device 104A or the orchestration service 102. Thus, absolute performance data (which is device specific) can be utilized by the workout device 104A and heart rate data (personal performance data) can also be utilized by the workout device 104A. In some embodiments, the controller 101 of the workout device 104A can also directly or indirectly measure the heart rate data of the individual.

As noted above, in addition to determining personal performance using heart rate calculations, the controller 101 of the workout device 104A can be configured to determine an aspect of personal performance using FTP. An example of personal performance includes calculating and using a power output threshold or maximum relative to a stationary bicycle. The power output threshold or maximum is indicative of a maximum amount of power that can be exerted by the individual on their workout device. In some embodiments, threshold performance values, whether absolute or personal, can be received by the controller 101 of the workout device 104A from the orchestration service 102.

In some embodiments, the power output threshold or maximum can be determined from a power output assessment routine (an example type of FTP analysis) that is executed at the workout device 104A. To be sure, other personal performance assessment routines can be used for other workout devices.

In some embodiments, the FTP can be determined by a maximal 20 minutes test (other time frames can also be utilized), to be performed on the workout device 104A prior to the user participating in a workout class. This data can be stored at the workout device 104A or in the orchestration service 102 used for the later workouts as a reference to determine the performance zones. The test comprises the user riding at a maximum effort (e.g., all out) for 20 minutes; then, the FTP is calculated as the 90% of the average power measured during the 20 minutes test.

It will be understood that the FTP value for a user changes as the user improves their physical conditioning through training. For example, the user can perform again the test after one month and an updated FTP value is stored and used as a new reference for the later workouts.

In one or more embodiments, the power output threshold or maximum for a stationary bicycle is determined using historical power output performance data obtained during the power output assessment routine. Again, these values can vary over time as the individual's performance parameters vary. Thus, in some embodiments, the real-time performance tracking module 105 is configured to compute or determine power output threshold or maximum using data collected during the power output assessment routine or from historical performance data obtained over time.

In various embodiments, the real-time performance tracking module 105 can calculate a power output percentage by dividing a real-time power output (e.g., real-time absolute performance data) generated by the individual at the workout device 104A with the power output threshold or maximum. For example, if an individual has a power output threshold or maximum of 200 watts and the individual has a real-time power output of 175 watts, the power output percentage is 87.5%.

According to some embodiments, the controller 101 of the workout device 104A is configured to use both absolute performance difference/percentage and heart rate difference/percentage in combination (through a comparative process) to assess an individual's current performance status for ranking purposes, as will be discussed in greater detail infra.

In addition to calculating the various performance metrics disclosed above, in various embodiments the controller 101 of the workout device 104A can receive video feeds (from the orchestration service 102) and generate unique graphical user interfaces, such as a graphical user interface 113 for display on an interface 115 of the workout device 104A. A detailed view of the graphical user interface 113 is illustrated and described in greater detail with reference to FIG. 4 (see graphical user interface 400 of FIG. 4).

In some embodiments, the real-time performance tracking module 105 can use the performance parameters and a performance assessment schema to determine a performance zone for an individual. In general, the performance zone can be determined using either absolute performance data or personal performance data. For example, this can include using the absolute performance difference or the personal performance difference values (e.g., comparisons of real-time data to baselines or thresholds).

In one example embodiment, the assessment schema includes a hierarchical or stratified mechanism or ranges that allow the real-time performance tracking module 105 to assign a performance zone to an individual. Aspects of how these performance zones are displayed or provided to the user are disclosed in greater detail below.

In various embodiments, the orchestration service 102 comprises a performance assessment module 108, a real-time performance tracking module 110, and a graphical user interface generator module 112. These modules provide the same and/or similar functions as the modules disclosed above with respect to the workout device controller 101.

Figure 2A:
FIG. 2A illustrates an example table of performance zones relative to treadmill performance (or other equivalent workout device).

FIG. 2A illustrates an example performance zone table 200 that represents a performance zone schema that can be used to determine a speed range reference for a user based on absolute performance data. It will be understood that the table 200 of FIG. 2A can be utilized with respect to determining user performance on a treadmill or other similar device.

In the table 200, a first color is associated with a speed range reference of approximately less than six km/h, a second color is associated with a speed range reference of approximately between six to eight km/h, a third color is associated with a speed range reference of approximately between eight to ten km/h, a fourth color is associated with a speed range reference of approximately between ten to twelve km/h, and a fifth color is associated with a speed range reference of approximately at or above twelve km/h. To be sure, while speed range references have been stratified into five levels, other embodiments allow for fewer or additional speed range reference levels. For example, these speed range references are used for determining which is the performance zone of the user at a certain time, in order to show the related color in the leaderboard, such as the leaderboard illustrated in FIGS. 1 and 4).

In some embodiments, as an alternative to color codes, other visual representations can be used. For example, images of animals may be used rather than, or in addition to, colors. For example, if the user's current speed is included in the range reference less than six km/h, an image of a snail may be illustrated in the leaderboard (again, see FIGS. 1 and 4). As the speed increases, different faster animals can be utilized (e.g. hare, cheetah and so on).

Also, while specific values for each level have been disclosed above, these values can be selectively adjusted by the user, a trainer, or in some embodiments automatically by a controller of the workout device.

Figure 2B:
FIG. 2B illustrates an example table of performance zones relative to bicycle performance.

FIG. 2B illustrates an example performance zone table 202 that represents a performance zone schema that can be used to determine a power range reference for a user based on absolute performance data. Rather than using speed range references, the table 202 measures performance based on power range references relative to user performance on a bicycle. In this example, the power range references are stratified into five levels, but as noted above, fewer or additional levels can be utilized.

It will be understood that table 202 of FIG. 2B refers to an example in which instantaneous power (an example absolute performance parameter) measured at a certain time during a workout is compared to reference power values (an example of absolute performance threshold), for example the values of table 200 of FIG. 2B. As a consequence, the same color (more or less the same power), does not mean the same effort level (e.g. color pink, for an advanced user could be a low intensity level while for a beginner user could be a very high intensity level).

Figure 3A:
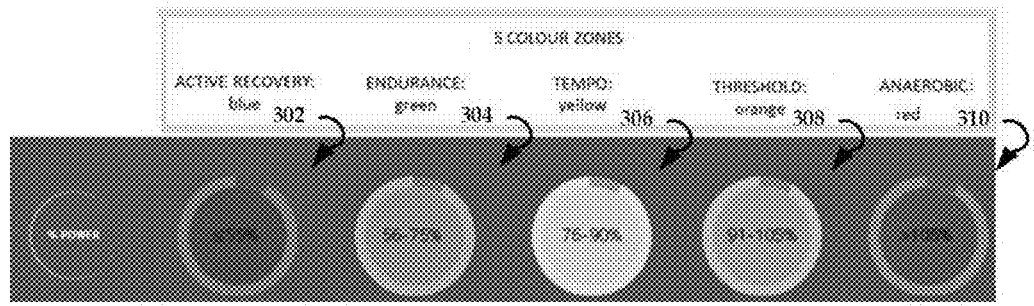
FIG. 3A illustrates another example graph of performance zones relative to FTP (Functional Threshold Power).
Figure 3B:
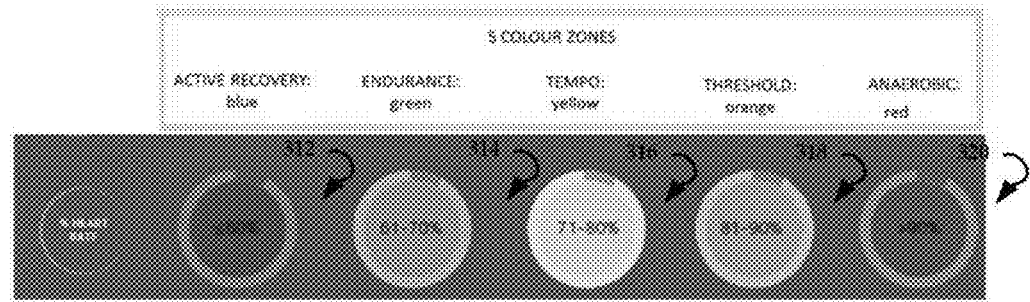
FIG. 3B illustrates another example graph of performance zones relative to heart rate zone maximum values.

FIGS. 3A and 3B each illustrates graphically an assessment schema where performance zones are separated by color based on heart rate percentage (personal performance in FIG. 3B) and/or power output percentage (personal performance in FIG. 3A) defined by value ranges. As noted above, the power output percentage is calculated by dividing a real-time power output generated by the individual at the workout device with the Functional Threshold Power (FTP) of the user, which has already been described supra. In FIG. 3A, a first performance zone 302 is associated with an active recovery performance zone. In the active recovery performance zone the power output percentage is at or below 55% of an individual's FTP. This active recovery performance zone is assigned a blue hue.

A second performance zone 304 is associated with an endurance performance zone. In the endurance performance zone the power output percentage is between approximately 56-75%, inclusive, of an individual's FTP. This endurance performance zone is assigned a green hue. A third performance zone 306 is associated with a tempo performance zone. In the tempo performance zone the power output percentage is between approximately 76-90%, inclusive, of an individual's FTP. This tempo performance zone is assigned a yellow hue.

A fourth performance zone 308 is associated with a threshold performance zone. In the threshold performance zone the power output percentage is between approximately 91-105%, inclusive, of an individual's FTP. This threshold performance zone is assigned an orange hue. A fifth performance zone 310 is associated with a VO2 max or anaerobic zone. In the VO2 max or anaerobic performance zone the power output percentage is above approximately 105% of an individual's FTP. This VO2 max or anaerobic zone performance zone is assigned a red hue.

In the embodiment in FIG. 3A, a personal performance threshold parameter is used as a reference: the FTP (Functional Threshold Power). For example, consider the following scenario: user1 has an FTP1 of 200 watts and user2 has an FTP2 of 150 watts. If during the workout user1 rides at 0 acts and user2 rides at 150 watts, the color illustrated would be orange for both (threshold level), despite the fact that the users are generating different power levels.

FIG. 3B illustrates another row of ranges which are indicative of a heart rate percentage of an individual. These values are percentages measured relative to a current heart rate level versus a maxima heart rate level for a user. A seventh performance zone 312 is associated with an active recovery performance zone. In the active recovery performance zone the heart rate percentage is at or below 60% of an individual's heart rate maximum. This active recovery performance zone is assigned a blue hue.

An eighth performance zone 314 is associated with an endurance performance zone. In the endurance performance zone the heart rate percentage is between approximately 61-70%, inclusive, of an individual's heart rate maximum. This endurance performance zone is assigned a green hue. A ninth performance zone 316 is associated with a tempo performance zone. In the tempo performance zone the heart rate percentage is between approximately 71-80%, inclusive, of an individual's heart rate maximum. This tempo performance zone is assigned a yellow hue.

A tenth performance zone 318 is associated with a threshold performance zone. In the threshold performance zone the heart rate percentage is between approximately 81-90%, inclusive, of an individual's heart rate maximum. This threshold performance zone is assigned an orange hue. An eleventh performance zone 320 is associated with a VO2 max or anaerobic zone. In the VO2 max or anaerobic performance zone the heart rate percentage is above approximately 90% of an individual's heart rate maximum. This VO2 max or anaerobic zone performance zone is assigned a red hue.

When the individual is training in the VO2 max or anaerobic performance zone the individual is potentially improving their VO2 max or anaerobic performance levels.

In various embodiments, the controller 101 of the workout device 104A is configured to perform these calculations and comparative evaluations relative to performance zones. Using the calculated or determined performance zone, the controller 101 of the workout device 104A can rank a plurality of individuals competing in real-time in a workout event.

Figure 4:
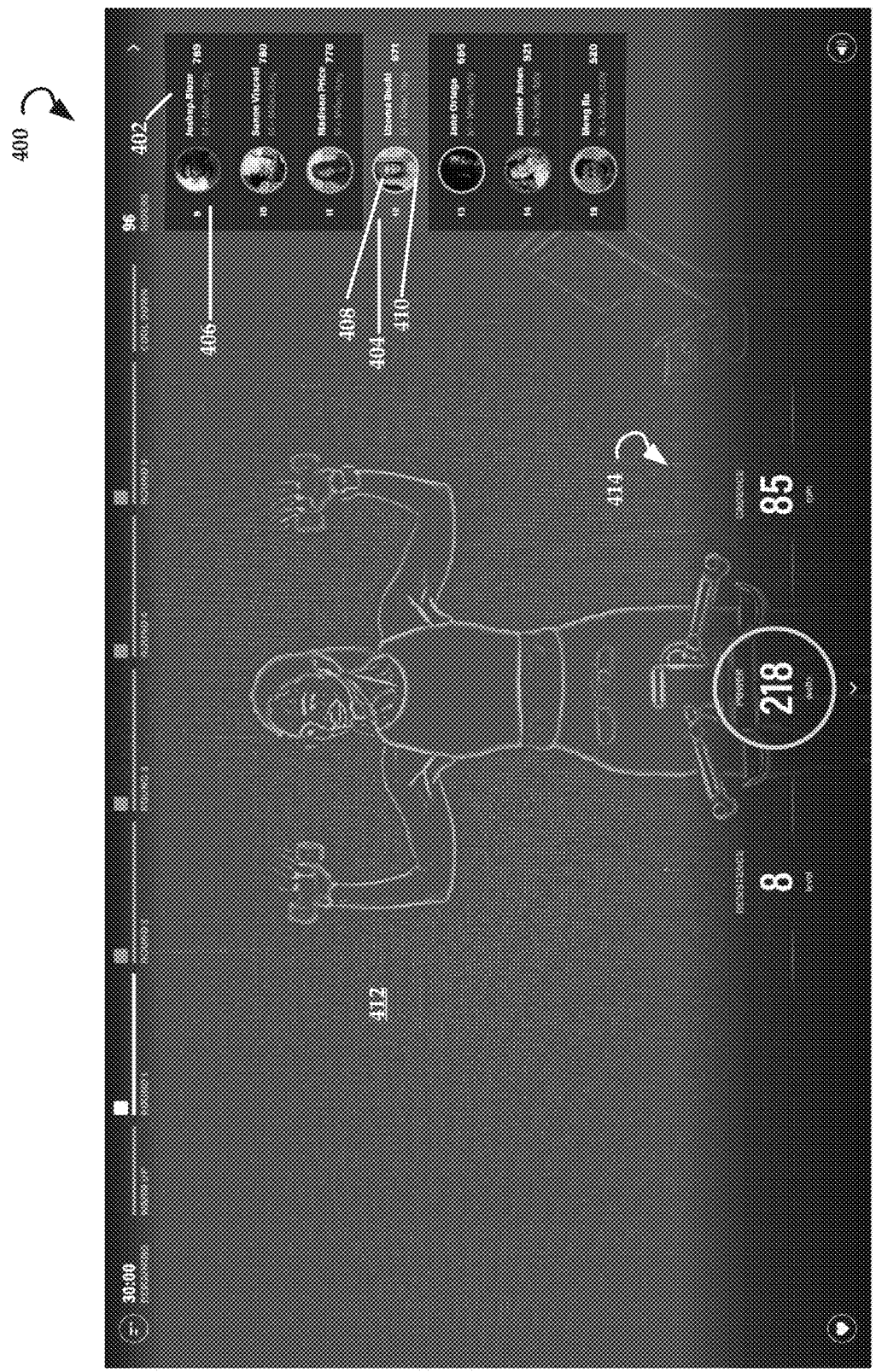
FIG. 4 illustrates an example interactive graphical user interface comprising a dynamic, real-time leaderboard.

FIG. 4 illustrates a graphical user interface 400 that includes a leaderboard 402 that includes entries that are ranked based on real-time performance zone assessment. The graphical user interface 400 and leaderboard 402 are generated for display by the graphical user interface generator module 107 of the controller 101 of the workout device 104A (see FIG. 1). To be sure, the data displayed on the graphical user interface 400 and leaderboard 402 includes real-time data. It will be understood that the leaderboard 402 comprises visual indications of the performance zones of a plurality of individuals, providing an instantaneous indication of relative performance and indicate potential upcoming changes in leaderboard positioning. Individuals can be apprised of their current ranking, but can also assess the current performance level of other competitors which may indicate if changes in the ranking are about to occur. In a non-limiting example, while Uzoma Buchi 404 is in fourth place on the leaderboard 402, this individual is likely to move up in ranking because they are in the tempo power zone compared to Joshep.Blaze 406, who is currently in first place on the leaderboard 402, but has reached his VO2 max or anaerobic performance zone. That is, as an individual moves through performance zones, the likelihood of sustaining a current performance level within the performance zones of threshold or VO2 max or anaerobic zone are unlikely. Thus, competitors can visually assess the performance level of their competitors relative to their own performance level to determine if they are likely to decrease or increase in ranking on the leaderboard 402.

In various embodiments, users or participants can be ranked in the leaderboard 402 based on any number of conditions such as total distance (e.g., total distance ran on a treadmill or total distance traveled on a bicycle), calories, calories expended per kilogram, average power over a time interval, actual power in real-time, or a metabolic equivalent value just to name a few. In some embodiments, more than one condition for ranking can be utilized. For example, the ranking of participants can be based on a combination of both total calories expended and any desired metabolic equivalent value.

Also, generally speaking, the controller 101 of the workout device 104A is configured to receive performance level metrics for other participants from the orchestration service 102 (see FIG. 1). The graphical user interface (GUI) generator module 107 can utilize the data received from the orchestration service 102 regarding other participants, in combination with the relevant performance level calculations for the user of the workout device 104A in order to generate the visual appearances of the users on the leaderboard 402 and rank the users based on their performance levels.

In order to allow for this visual assessment, each entry on the leaderboard 402 is associated with information gathered from the workout devices in real-time. For example, an entry associated with Uzoma Buchi 404 includes a username "Uzoma Buchi" and an icon 408 that comprises a hue that is associated with Julia's current performance zone/level. In this instance, Uzoma Buchi is in the tempo performance zone. In contrast, Joshep.Blaze 406 is associated with the VO2 max or anaerobic zone. Thus, Uzoma Buchi 404 can conclude that Joshep.Blaze 406 is about to slow down, thus indicating a potential change in leaderboard position.

In some embodiments, the icon 408 can include an image selected by the individual. According to some embodiments, the performance zone is indicated using a colored arcuate indicator 410 that concentrically surrounds the icon 408. In some embodiments, the colored arcuate indicator 410 comprises the hue that is associated with the real-time performance zone/level for the individual.

In addition to the leaderboard 402, the graphical user interface 400 comprises a broadcast or simulcast of a real-time video 412 of an instructor leading a workout. As the individuals are performing the workout, additional workout or performance related data is transmitted from the workout devices to the orchestration service. For example, performance data regarding heart rate, heart rate percentage, a resistance level for a workout device, a cadence, or combinations thereof can be displayed on the graphical user interface 400. In some embodiments, these data are displayed in a ribbon or bar 414 located near a bottom portion of the graphical user interface 400. In other embodiments, the graphical user interface 400 can also include indications of any of caloric expenditure, speed, or combinations thereof. The graphical user interface 400 can also display maximum and average values for any of the performance data disclosed as well.

In various embodiments, the graphical user interface 400 can also include workout specific information and graphics such as timer that displays a remaining time for a workout, as well as a diagrammatical view of the workout separated into stages or rounds. A highlighted one of the stages or rounds will indicate to a user what stage or round in which they are participating.

In some embodiments, users can filter the leaderboard 402 such that only users with certain demographic information are illustrated in the leaderboard 402. For example, a user can select that they only wish to see other users presented in the leaderboard 402 that are in a specific age range. For example, the user can specific that the leaderboard 402 should only include icons for other participants in their 30s. In another example, the user can specific that the leaderboard 402 should only include icons for other participants who have a VO2 max that is approximately the same as the user's VO2 max.

Figure 5:
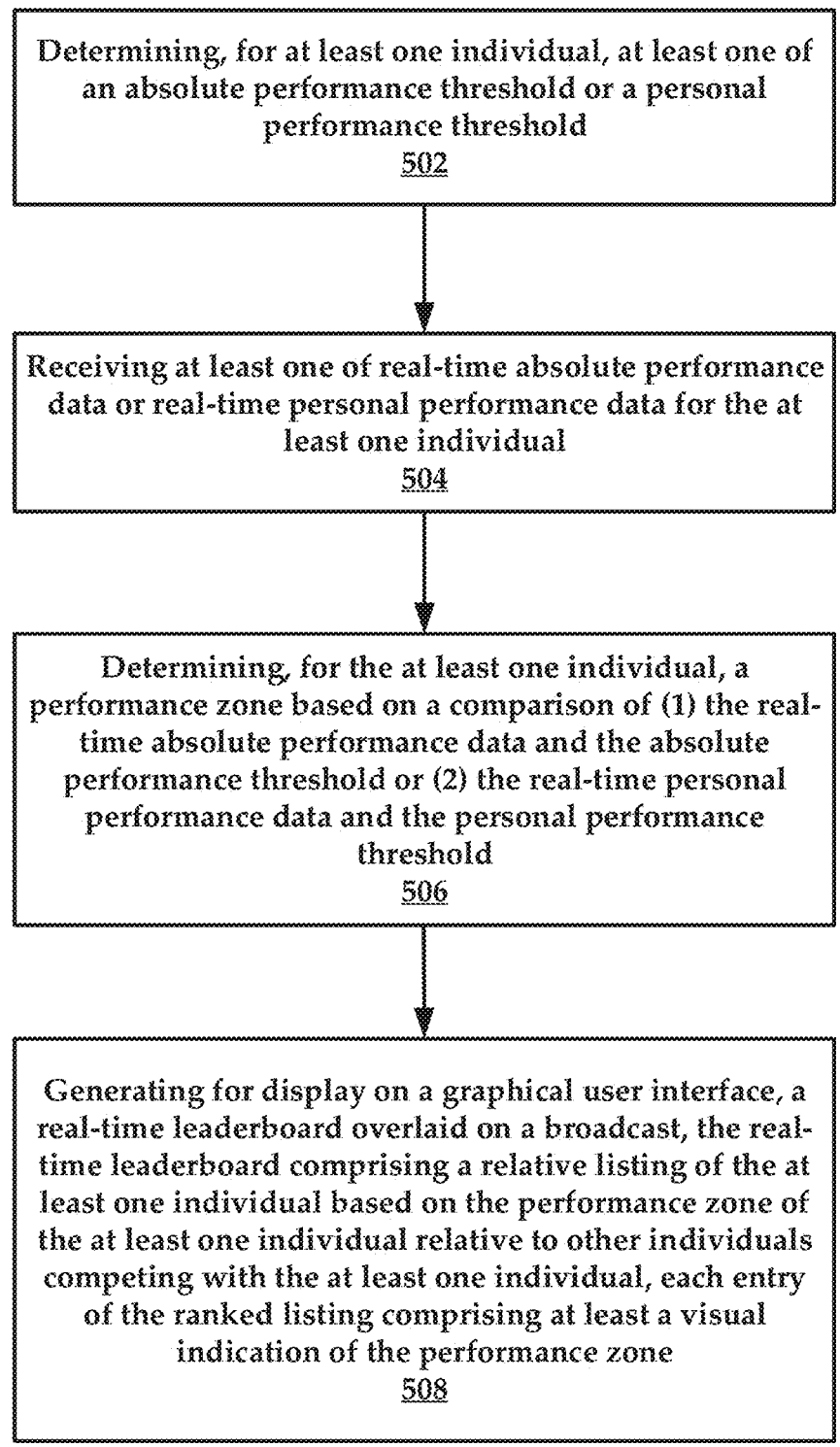
FIG. 5 is a flowchart of an example method of the present disclosure.

FIG. 5 is a flowchart of an example method of the present disclosure. This method can be performed by controller 101 of the workout device 104A (see FIG. 1). In some embodiments, the method can be performed by the orchestration service 102, with corresponding displays of graphical user interfaces occurring at the workout device. In these embodiments, the orchestration service and the workout device can cooperate in a server-client relationship.

Initially, each individual can register with an orchestration service of the present disclosure. The orchestration service can create an account or record for each individual. The account can include data gathered through an interface on a workout device, such as a smart stationary bicycle. The user can enter physical or demographic data such as age, height, weight, and so forth. The individual can also input any data required to assess performance thresholds for the individual. This can include any data required to calculate or estimate a maximum heart rate or maximum power output (i.e., FTP) for the individual. Thus, in this example the method includes a step 502 of determining, for at least one individual, at least one of an absolute performance threshold or a personal performance threshold. This can include the workout device receiving an absolute performance threshold or a personal performance threshold for a user from the orchestration service. In other embodiments, these values can be assessed from a routine executed at the workout device.

Once these absolute and/or personal performance thresholds have been determined or received, the method can transition to a tracking phase where individuals are tracked and assessed during a workout or other competitive event.

In various embodiments, the method includes a step 504 of receiving at least one of real-time absolute performance data or real-time personal performance data. As noted above, the performance parameters can include any aspect of performance that is received while an individual is participating in a competitive event such as a workout.

Next, the method includes a step 506 of determining a performance zone for the at least one individual based on (1) a comparison between the real-time absolute performance data and the absolute performance threshold or (2) a comparison between the real-time personal performance data and the personal performance threshold.

In some embodiments, the current heart rate is utilized in conjunction with a heart rate maximum value calculated for the individual. As noted above, this could include calculating or estimating a maximum heart rate for the individual. Thus, the performance zone is based on the heart rate percentage, which is a function of the heart rate as a percentage of the maximum heart rate for the individual. In other embodiments, the performance zone is based on both the heart rate percentage and the power output percentage (or FTP).

As the current performance zone is determined for each individual, the method includes a step 508 of generating for display on a graphical user interface, a real-time leaderboard overlaid on a broadcast. In various embodiments, the real-time leaderboard comprises a relative listing of the at least one individual based on the performance zone of the at least one individual relative to other individuals competing with the at least one individual. In some embodiments, each entry of the relative/ranked listing comprises at least a visual indication of the performance zone, where the visual indication is generated by the workout device. Example visual indications are illustrated in FIG. 4. It will be understood that the visual indications of the leaderboard provide an instantaneous indication of relative performance of the individuals and indicating potential upcoming changes in leaderboard positioning.

Figure 6:
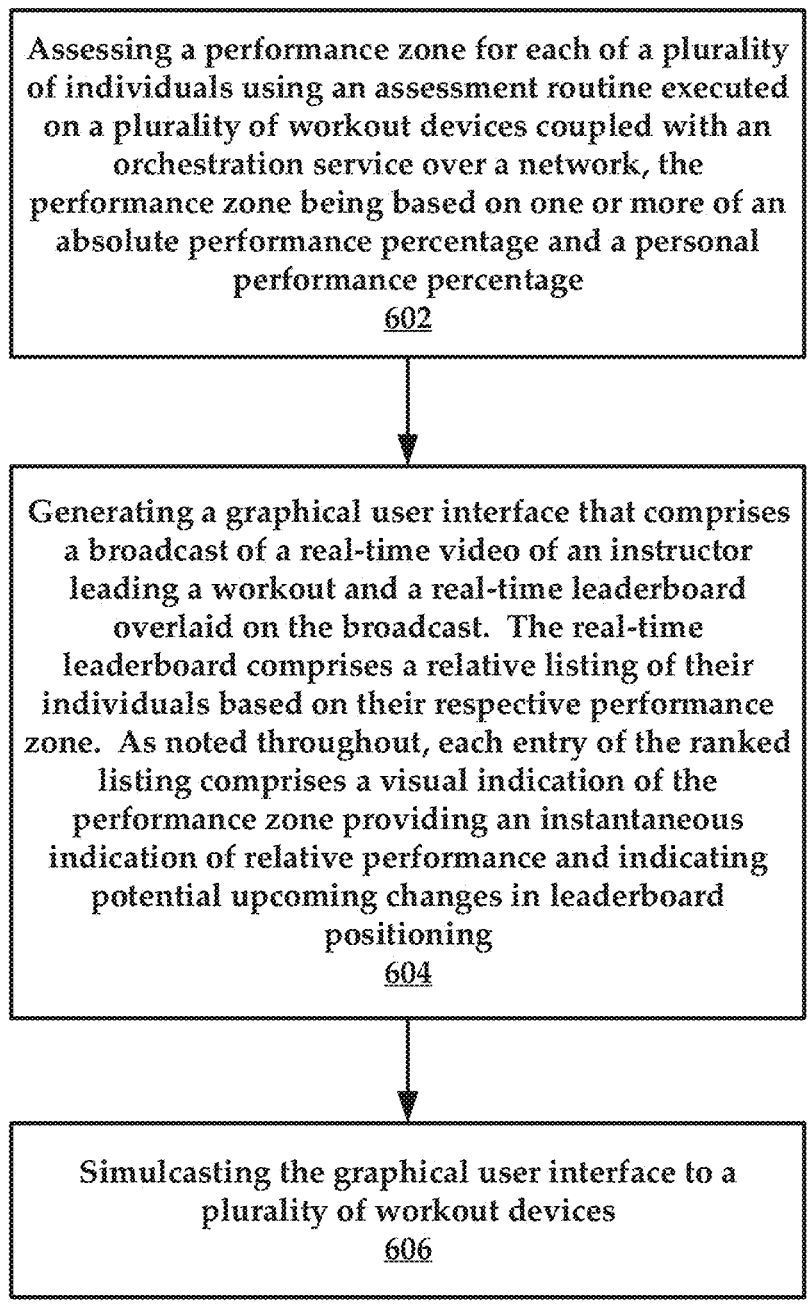
FIG. 6 is a flowchart of another example method of the present disclosure.

FIG. 6 is a flowchart of another example method of the present disclosure. The method includes a step 602 of assessing a performance zone for each of a plurality of individuals using an assessment routine executed on a plurality of workout devices coupled with an orchestration service over a network. In some embodiments, the performance zone is based on one or more of an absolute performance percentage and a personal performance percentage.

It will be understood that concerning heart rate calculations, a Maximum Heart Rate (HRmax) of an individual (rather than estimate it by the formula 220–age) can be determined by a test performed by the individual on the exercise machine (bike or treadmill for example), as disclosed supra. To determine an accurate value of the HRmax, a "Maximal Test" can be performed which comprises measuring the oxygen consumption of the user (with a device called Gas Analyzer) during a workout at a maximum effort level for the individual until the individual cannot exercise any further. Then, the maximum heart rate of the user is calculated by an algorithm. When the requisite instruments are not available for this type of testing, the present disclosure contemplates utilizing a test in which the heart rate is measured and a HRmax is calculated by a specific algorithm.

It will be understood that concerning power calculations, such as FTP, an example test for determining the FTP is described supra, which is a personal performance threshold specific for a workout device such as a stationary bicycle.

Once these performance zones have been assessed and a workout is occurring, the method includes a step 604 of generating a graphical user interface that comprises a broadcast of a real-time video of an instructor leading a workout and a real-time leaderboard overlaid on the broadcast. The real-time leaderboard comprises a relative listing of their individuals based on their respective performance zone calculated using their performance threshold. As noted throughout, each entry of the relative/ranked listing comprises a visual indication of the performance zone providing an instantaneous indication of relative performance and indicating potential upcoming changes in leaderboard positioning. Additionally, the method can include a step 606 of simulcasting the graphical user interface to a plurality of workout devices.

Figure 7:
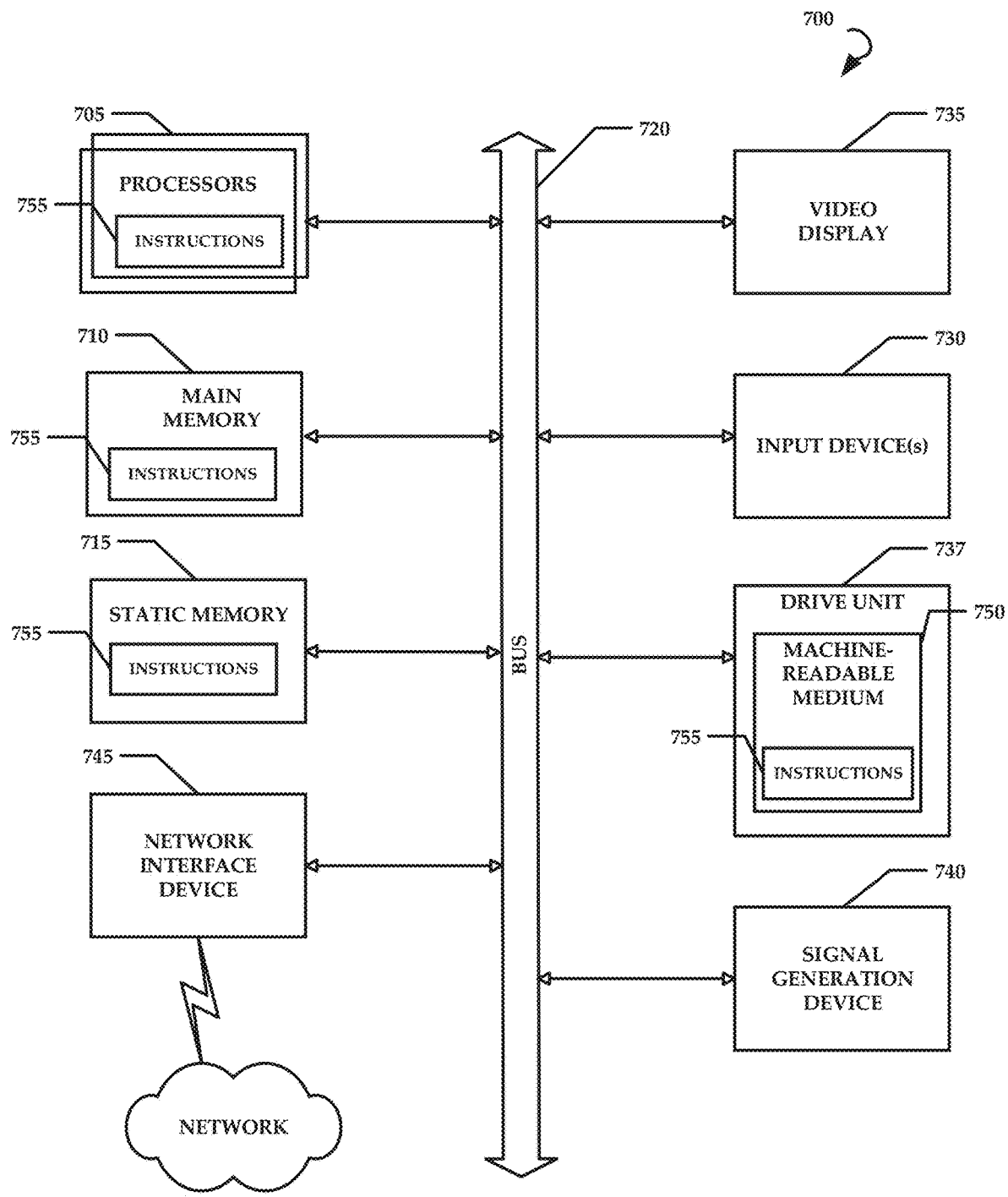
FIG. 7 is a diagrammatic representation of an example machine in the form of a computer system.

FIG. 7 is a diagrammatic representation of an example machine in the form of a computer system 700, within which a set of instructions for causing the machine to perform any one or more of the methodologies discussed herein may be executed. In various example embodiments, the machine operates as a standalone device or may be connected (e.g., networked) to other machines. In a networked deployment, the machine may operate in the capacity of a server or a client machine in a server-client network environment, or as a peer machine in a peer-to-peer (or distributed) network environment. The machine may be a personal computer (PC), a tablet PC, a set-top box (STB), a personal digital assistant (PDA), a cellular telephone, a portable music player (e.g., a portable hard drive audio device such as an Moving Picture Experts Group Audio Layer 3 (MP3) player), a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 700 includes a processor or multiple processor(s) 705 (e.g., a central processing unit (CPU), a graphics processing unit (GPU), or both), and a main memory 710 and static memory 715, which communicate with each other via a bus 720. The computer system 700 may further include a video display 735 (e.g., a liquid crystal display (LCD)). The computer system 700 may also include an alpha-numeric input device(s) 730 (e.g., a keyboard), a cursor control device (e.g., a mouse), a voice recognition or biometric verification unit (not shown), a disk drive unit 737 (also referred to as disk drive unit), a signal generation device 740 (e.g., a speaker), and a network interface device 745. The computer system 700 may further include a data encryption module (not shown) to encrypt data.

The disk drive unit 737 includes a computer or machine-readable medium 750 on which is stored one or more sets of instructions and data structures (e.g., instructions 755) embodying or utilizing any one or more of the methodologies or functions described herein. The instructions 755 may also reside, completely or at least partially, within the main memory 710 and/or within the processor(s) 705 during execution thereof by the computer system 700. The main memory 710 and the processor(s) 705 may also constitute machine-readable media.

The instructions 755 may further be transmitted or received over a network via the network interface device 745 utilizing any one of a number of well-known transfer protocols (e.g., Hyper Text Transfer Protocol (HTTP)). While the machine-readable medium 750 is shown in an example embodiment to be a single medium, the term "computer-readable medium" should be taken to include a single medium or multiple media (e.g., a centralized or distributed database and/or associated caches and servers) that store the one or more sets of instructions. The term "computer-readable medium" shall also be taken to include any medium that is capable of storing, encoding, or carrying a set of instructions for execution by the machine and that causes the machine to perform any one or more of the methodologies of the present application, or that is capable of storing, encoding, or carrying data structures utilized by or associated with such a set of instructions. The term "computer-readable medium" shall accordingly be taken to include, but not be limited to, solid-state memories, optical and magnetic media, and carrier wave signals. Such media may also include, without limitation, hard disks, floppy disks, flash memory cards, digital video disks, random access memory (RAM), read only memory (ROM), and the like. The example embodiments described herein may be implemented in an operating environment comprising software installed on a computer, in hardware, or in a combination of software and hardware.

One skilled in the art will recognize that the Internet service may be configured to provide Internet access to one or more computing devices that are coupled to the Internet service, and that the computing devices may include one or more processors, buses, memory devices, display devices, input/output devices, and the like. Furthermore, those skilled in the art may appreciate that the Internet service may be coupled to one or more databases, repositories, servers, and the like, which may be utilized in order to implement any of the embodiments of the disclosure as described herein.

The corresponding structures, materials, acts, and equivalents of all means or step plus function elements in the claims below are intended to include any structure, material, or act for performing the function in combination with other claimed elements as specifically claimed. The description of the present technology has been presented for purposes of illustration and description, but is not intended to be exhaustive or limited to the present technology in the form disclosed. Many modifications and variations will be apparent to those of ordinary skill in the art without departing from the scope and spirit of the present technology. Exemplary embodiments were chosen and described in order to best explain the principles of the present technology and its practical application, and to enable others of ordinary skill in the art to understand the present technology for various embodiments with various modifications as are suited to the particular use contemplated.

Aspects of the present technology are described above with reference to flowchart illustrations and/or block diagrams of methods, apparatus (systems) and computer program products according to embodiments of the present technology. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

In the following description, for purposes of explanation and not limitation, specific details are set forth, such as particular embodiments, procedures, techniques, etc. in order to provide a thorough understanding of the present invention. However, it will be apparent to one skilled in the art that the present invention may be practiced in other embodiments that depart from these specific details.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" or "according to one embodiment" (or other phrases having similar import) at various places throughout this specification are not necessarily all referring to the same embodiment. Furthermore, the particular features, structures, or characteristics may be combined in any suitable manner in one or more embodiments. Furthermore, depending on the context of discussion herein, a singular term may include its plural forms and a plural term may include its singular form. Similarly, a hyphenated term (e.g., "on-demand") may be occasionally interchangeably used with its non-hyphenated version (e.g., "on demand"), a capitalized entry (e.g., "Software") may be interchangeably used with its non-capitalized version (e.g., "software"), a plural term may be indicated with or without an apostrophe (e.g., PE's or PEs), and an italicized term (e.g., "N+1") may be interchangeably used with its non-italicized version (e.g., "N+1"). Such occasional interchangeable uses shall not be considered inconsistent with each other.

Also, some embodiments may be described in terms of "means for" performing a task or set of tasks. It will be understood that a "means for" may be expressed herein in terms of a structure, such as a processor, a memory, an I/O device such as a camera, or combinations thereof. Alternatively, the "means for" may include an algorithm that is descriptive of a function or method step, while in yet other embodiments the "means for" is expressed in terms of a mathematical formula, prose, or as a flow chart or signal diagram.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It is noted at the outset that the terms "coupled," "connected", "connecting," "electrically connected," etc., are used interchangeably herein to generally refer to the condition of being electrically/electronically connected. Similarly, a first entity is considered to be in "communication" with a second entity (or entities) when the first entity electrically sends and/or receives (whether through wireline or wireless means) information signals (whether containing data information or non-data/control information) to the second entity regardless of the type (analog or digital) of those signals. It is further noted that various figures (including component diagrams) shown and discussed herein are for illustrative purpose only, and are not drawn to scale.

If any disclosures are incorporated herein by reference and such incorporated disclosures conflict in part and/or in whole with the present disclosure, then to the extent of conflict, and/or broader disclosure, and/or broader definition of terms, the present disclosure controls. If such incorporated disclosures conflict in part and/or in whole with one another, then to the extent of conflict, the later-dated disclosure controls.

The terminology used herein can imply direct or indirect, full or partial, temporary or permanent, immediate or delayed, synchronous or asynchronous, action or inaction. For example, when an element is referred to as being "on," "connected" or "coupled" to another element, then the element can be directly on, connected or coupled to the other element and/or intervening elements may be present, including indirect and/or direct variants. In contrast, when an element is referred to as being "directly connected" or "directly coupled" to another element, there are no intervening elements present.

Although the terms first, second, etc. may be used herein to describe various elements, components, regions, layers and/or sections, these elements, components, regions, layers and/or sections should not necessarily be limited by such terms. These terms are only used to distinguish one element, component, region, layer or section from another element, component, region, layer or section. Thus, a first element, component, region, layer or section discussed below could be termed a second element, component, region, layer or section without departing from the teachings of the present disclosure.

The terminology used herein is for the purpose of describing particular embodiments only and is not intended to be necessarily limiting of the disclosure. As used herein, the singular forms "a," "an" and "the" are intended to include the plural forms as well, unless the context clearly indicates otherwise. The terms "comprises," "includes" and/or "comprising," "including" when used in this specification, specify the presence of stated features, integers, steps, operations, elements, and/or components, but do not preclude the presence or addition of one or more other features, integers, steps, operations, elements, components, and/or groups thereof.

Example embodiments of the present disclosure are described herein with reference to illustrations of idealized embodiments (and intermediate structures) of the present disclosure. As such, variations from the shapes of the illustrations as a result, for example, of manufacturing techniques and/or tolerances, are to be expected. Thus, the example embodiments of the present disclosure should not be construed as necessarily limited to the particular shapes of regions illustrated herein, but are to include deviations in shapes that result, for example, from manufacturing.

Any and/or all elements, as disclosed herein, can be formed from a same, structurally continuous piece, such as being unitary, and/or be separately manufactured and/or connected, such as being an assembly and/or modules. Any and/or all elements, as disclosed herein, can be manufactured via any manufacturing processes, whether additive manufacturing, subtractive manufacturing and/or other any other types of manufacturing. For example, some manufacturing processes include three dimensional (3D) printing, laser cutting, computer numerical control (CNC) routing, milling, pressing, stamping, vacuum forming, hydroforming, injection molding, lithography and/or others.

Any and/or all elements, as disclosed herein, can include, whether partially and/or fully, a solid, including a metal, a mineral, a ceramic, an amorphous solid, such as glass, a glass ceramic, an organic solid, such as wood and/or a polymer, such as rubber, a composite material, a semiconductor, a nano-material, a biomaterial and/or any combinations thereof. Any and/or all elements, as disclosed herein, can include, whether partially and/or fully, a coating, including an informational coating, such as ink, an adhesive coating, a melt-adhesive coating, such as vacuum seal and/or heat seal, a release coating, such as tape liner, a low surface energy coating, an optical coating, such as for tint, color, hue, saturation, tone, shade, transparency, translucency, non-transparency, luminescence, anti-reflection and/or holographic, a photo-sensitive coating, an electronic and/or thermal property coating, such as for passivity, insulation, resistance or conduction, a magnetic coating, a water-resistant and/or waterproof coating, a scent coating and/or any combinations thereof.

Unless otherwise defined, all terms (including technical and scientific terms) used herein have the same meaning as commonly understood by one of ordinary skill in the art to which this disclosure belongs. The terms, such as those defined in commonly used dictionaries, should be interpreted as having a meaning that is consistent with their meaning in the context of the relevant art and should not be interpreted in an idealized and/or overly formal sense unless expressly so defined herein.

Furthermore, relative terms such as "below," "lower," "above," and "upper" may be used herein to describe one element's relationship to another element as illustrated in the accompanying drawings. Such relative terms are intended to encompass different orientations of illustrated technologies in addition to the orientation depicted in the accompanying drawings. For example, if a device in the accompanying drawings is turned over, then the elements described as being on the "lower" side of other elements would then be oriented on "upper" sides of the other elements. Similarly, if the device in one of the figures is turned over, elements described as "below" or "beneath" other elements would then be oriented "above" the other elements. Therefore, the example terms "below" and "lower" can, therefore, encompass both an orientation of above and below.

While various embodiments have been described above, it should be understood that they have been presented by way of example only, and not limitation. The descriptions are not intended to limit the scope of the invention to the particular forms set forth herein. To the contrary, the present descriptions are intended to cover such alternatives, modifications, and equivalents as may be included within the spirit and scope of the invention as defined by the appended claims and otherwise appreciated by one of ordinary skill in the art. Thus, the breadth and scope of a preferred embodiment should not be limited by any of the above-described exemplary embodiments.

What is claimed is:

1. A method, comprising:
   determining, for at least one individual, at least one of an absolute performance threshold or a personal performance threshold;
   receiving at least one of real-time absolute performance data or real-time personal performance data for the at least one individual;
   determining, for the at least one individual, a performance zone based on a comparison of the real-time personal performance data and the personal performance threshold; and
   generating for display on a graphical user interface:
      a real-time leaderboard overlaid on a broadcast, the real-time leaderboard comprising a relative listing of the at least one individual based on the performance zone of the at least one individual relative to other individuals competing with the at least one individual, each entry of the relative listing comprising at least a visual indication of the performance zone, wherein each entry comprises a username and an icon that comprises a hue.

2. The method according to claim 1, wherein determining the performance zone further comparing the real-time absolute performance data and the absolute performance threshold.

3. The method according to claim 1, wherein the performance zone is one of a plurality of performance zones, each performance zone being associated with a hue.

4. The method according to claim 3, wherein each entry comprises the username, the icon, and an arcuate indicator that concentrically surrounds the icon, the arcuate indicator comprising the hue.

5. The method according to claim 1, wherein the graphical user interface further comprises a centralized indicator that illustrates a power output and the performance zone for the at least one individual.

6. The method according to claim 1, wherein the graphical user interface further comprises an indication of any of a heart rate and a heart rate percentage, a resistance level for a workout device, a cadence, or combinations thereof.

7. The method according to claim 6, wherein the graphical user interface further comprises an indication of any of caloric expenditure, speed, or combinations thereof.

8. The method according to claim 1, wherein the absolute performance threshold is a measurement of work performed on a workout device by an individual.

9. A system, comprising:
   a processor and memory, the processor being configured to execute instructions stored in the memory to:
      determine, for each of a plurality of individuals, at least one of an absolute performance threshold or a personal performance threshold;

receive a data feed from each of a plurality of workout devices associated with the plurality of individuals over a network, the data feed comprising at least one of real-time absolute performance data or real-time personal performance data;

determine, for each of the plurality of individuals, a performance zone based on at least one of a combination of the real-time absolute performance data and the absolute performance threshold or a combination of the real-time personal performance data and the personal performance threshold; and provide a graphical user interface that comprises:
  a broadcast of a real-time video of an instructor leading a workout; and
  a real-time leaderboard overlaid on the broadcast, the real-time leaderboard comprising a relative listing of the plurality of individuals based on the performance zone of each of the plurality of individuals, each entry of the relative listing comprising a visual indication of the performance zone providing an instantaneous indication of relative performance of the plurality of individuals and indicate potential upcoming changes in leaderboard positioning, wherein each entry comprises a username and an icon that comprises a hue.

10. The system according to claim 9, wherein the absolute performance threshold is a measurement of work performed on a workout device by an individual.

11. The system according to claim 9, wherein the performance zone is one of a plurality of performance zones, each performance zone being associated with a hue.

12. The system according to claim 11, wherein each entry comprises the username, the icon, and an arcuate indicator that concentrically surrounds the icon, the arcuate indicator comprising the hue.

13. The system according to claim 9, wherein the graphical user interface further comprises a centralized indicator that illustrates a power output and the performance zone for an individual.

14. The system according to claim 9, wherein the graphical user interface further comprises an indication of any of heart rate, heart rate percentage, a resistance level for a workout device, a cadence, or combinations thereof.

15. The system according to claim 14, wherein the graphical user interface further comprises an indication of any of caloric expenditure, speed, or combinations thereof.

16. A method, comprising:
assessing a performance zone for each of a plurality of individuals using an assessment routine executed on a plurality of workout devices coupled with an orchestration service over a network, the performance zone being based on one or more of an absolute performance percentage and a personal performance percentage;
generating a graphical user interface that comprises:
  a broadcast of a real-time video of an instructor leading a workout; and
  a real-time leaderboard overlaid on the broadcast, the real-time leaderboard comprising a relative listing of the plurality of individuals based on their respective performance zone, each entry of the relative listing comprising a visual indication of the performance zone providing an instantaneous indication of relative performance of the plurality of individuals and indicating potential upcoming changes in leaderboard positioning;
simulcasting the graphical user interface to the plurality of workout devices; and
receiving a data feed from each of the plurality of workout devices over a network, the data feed comprising real-time absolute performance data or real-time personal performance data.

17. The method according to claim 16, wherein the absolute performance percentage is based on power output.

18. A method, comprising:
determining, for at least one individual, at least one of an absolute performance threshold or a personal performance threshold;
receiving at least one of real-time absolute performance data or real-time personal performance data for the at least one individual;
determining, for the at least one individual, a performance zone based on a comparison of the real-time personal performance data and the personal performance threshold; and
generating for display on a graphical user interface:
  a real-time leaderboard overlaid on a broadcast, the real-time leaderboard comprising a relative listing of the at least one individual based on the performance zone of the at least one individual relative to other individuals competing with the at least one individual, each entry of the relative listing comprising at least a visual indication of the performance zone, wherein the performance zone is one of a plurality of performance zones, each performance zone being associated with a hue, and wherein each entry comprises a username, an icon, and an arcuate indicator that concentrically surrounds the icon, the arcuate indicator comprising the hue.

19. The method according to claim 18, wherein the graphical user interface further comprises a centralized indicator that illustrates a power output and the performance zone for the at least one individual.

20. The method according to claim 18, wherein the graphical user interface further comprises an indication of any of a heart rate and a heart rate percentage, a resistance level for a workout device, a cadence, or combinations thereof.

* * * * *